United States Patent [19]

Sakurai et al.

[11] Patent Number: 5,582,588
[45] Date of Patent: Dec. 10, 1996

[54] ULTRASONIC THERAPEUTIC APPARATUS

[75] Inventors: Tomohisa Sakurai; Yukiko Nagaoka; Tetsumaru Kubota; Yuichi Ikeda, all of Tokyo, Japan

[73] Assignee: Olympus Optical Co., Ltd., Tokyo, Japan

[21] Appl. No.: 393,379

[22] Filed: Feb. 23, 1995

Related U.S. Application Data

[62] Division of Ser. No. 166,520, Dec. 13, 1993, Pat. No. 5,462,522.

[30] Foreign Application Priority Data

Apr. 19, 1993 [JP] Japan ................ 5-91587

[51] Int. Cl.$^6$ ............................................. A61B 17/20
[52] U.S. Cl. ...................................................... 604/22
[58] Field of Search .................................. 604/22; 606/32, 606/39, 45; 601/2; 607/96, 97, 101, 113, 102, 115, 116; 128/DIG. 13, DIG. 12

[56] References Cited

U.S. PATENT DOCUMENTS

| | | | |
|---|---|---|---|
| 5,011,471 | 4/1991 | Miyazaki et al. | 604/22 |
| 5,027,792 | 7/1991 | Mayer | 604/22 |
| 5,042,460 | 8/1991 | Sakurai et al. | |
| 5,076,276 | 12/1991 | Sakurai et al. | |
| 5,151,085 | 9/1992 | Sakurai et al. | |
| 5,154,723 | 10/1992 | Kubota et al. | |
| 5,188,102 | 2/1993 | Idemoto et al. | 604/22 |
| 5,211,625 | 5/1993 | Sakurai et al. | 604/22 |
| 5,255,669 | 10/1993 | Kubota et al. | 604/22 |

FOREIGN PATENT DOCUMENTS

| | | |
|---|---|---|
| 4-158856 | 6/1992 | Japan . |
| 5-168697 | 7/1993 | Japan . |

*Primary Examiner*—Manuel Mendez
*Attorney, Agent, or Firm*—Frishauf, Holtz, Goodman, Langer & Chick

[57] ABSTRACT

An ultrasonic therapeutic apparatus comprising an apparatus body including a drive source for ultrasonic oscillation, a hand piece including an ultrasonic vibrator and removably connected to the apparatus body, a drive unit in the apparatus body for applying voltage to the ultrasonic vibrator of the hand piece, thereby driving the ultrasonic vibrator, a probe removably connected to the hand piece and adapted to be vibrated by ultrasonic vibration produced as the ultrasonic vibrator is driven, thereby treating organic tissue, a water supply unit for supplying cooling water to cool the probe, a suction unit for removing waste matter by suction from the organic tissue treated by means of the cooling water and the probe, an ultrasonic output setting section for setting a preset value for an ultrasonic output from the ultrasonic vibrator, a feedwater output setting section for setting a preset value for a feedwater output from the water supply unit, a feedwater output control section for controlling the feedwater output setting by the feedwater output setting section so that the preset feedwater output value is a value such that the probe is cooled and is not excessively heated, and a memory unit for storing the preset values for the ultrasonic output and the feedwater output.

3 Claims, 13 Drawing Sheets

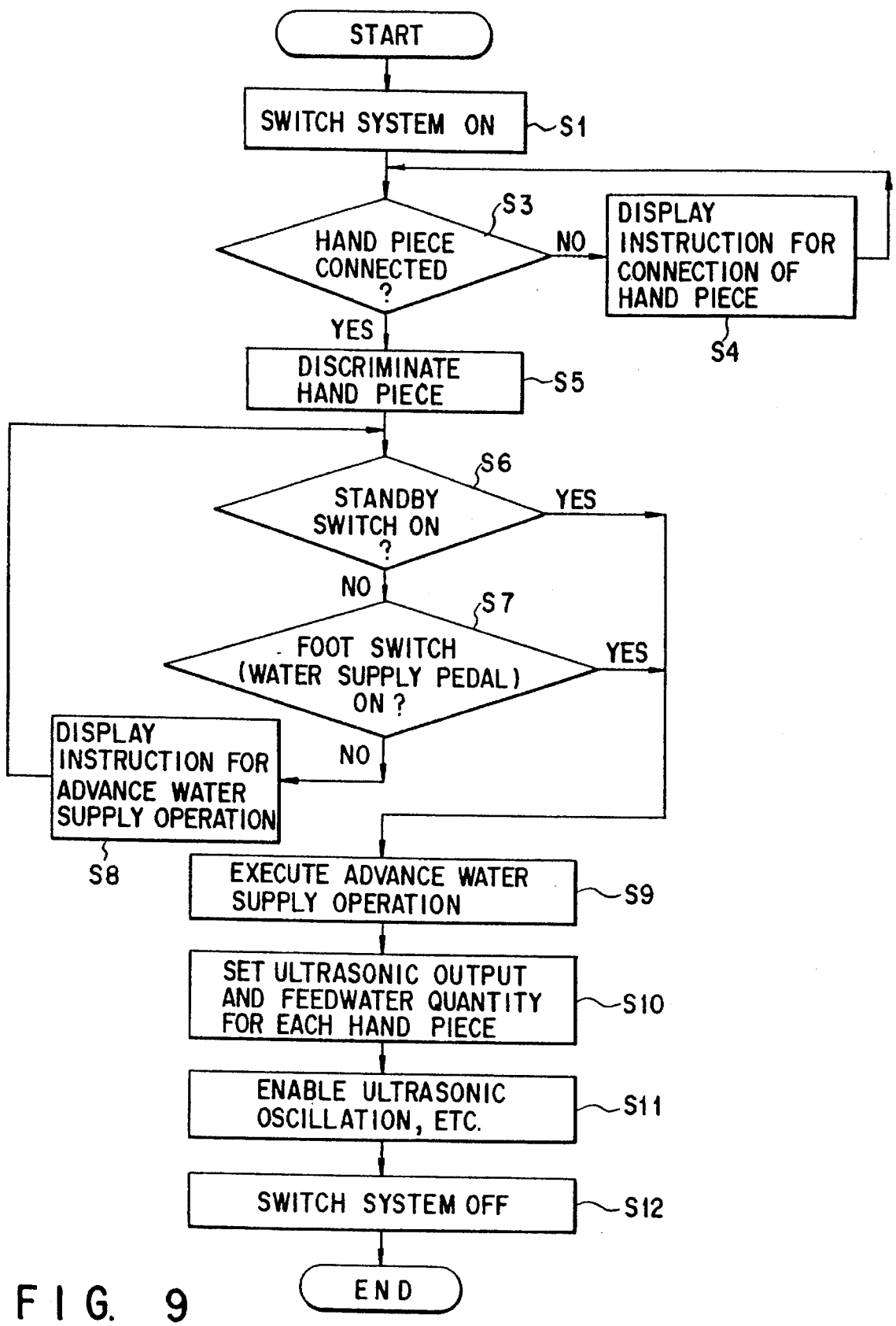
F I G. 9

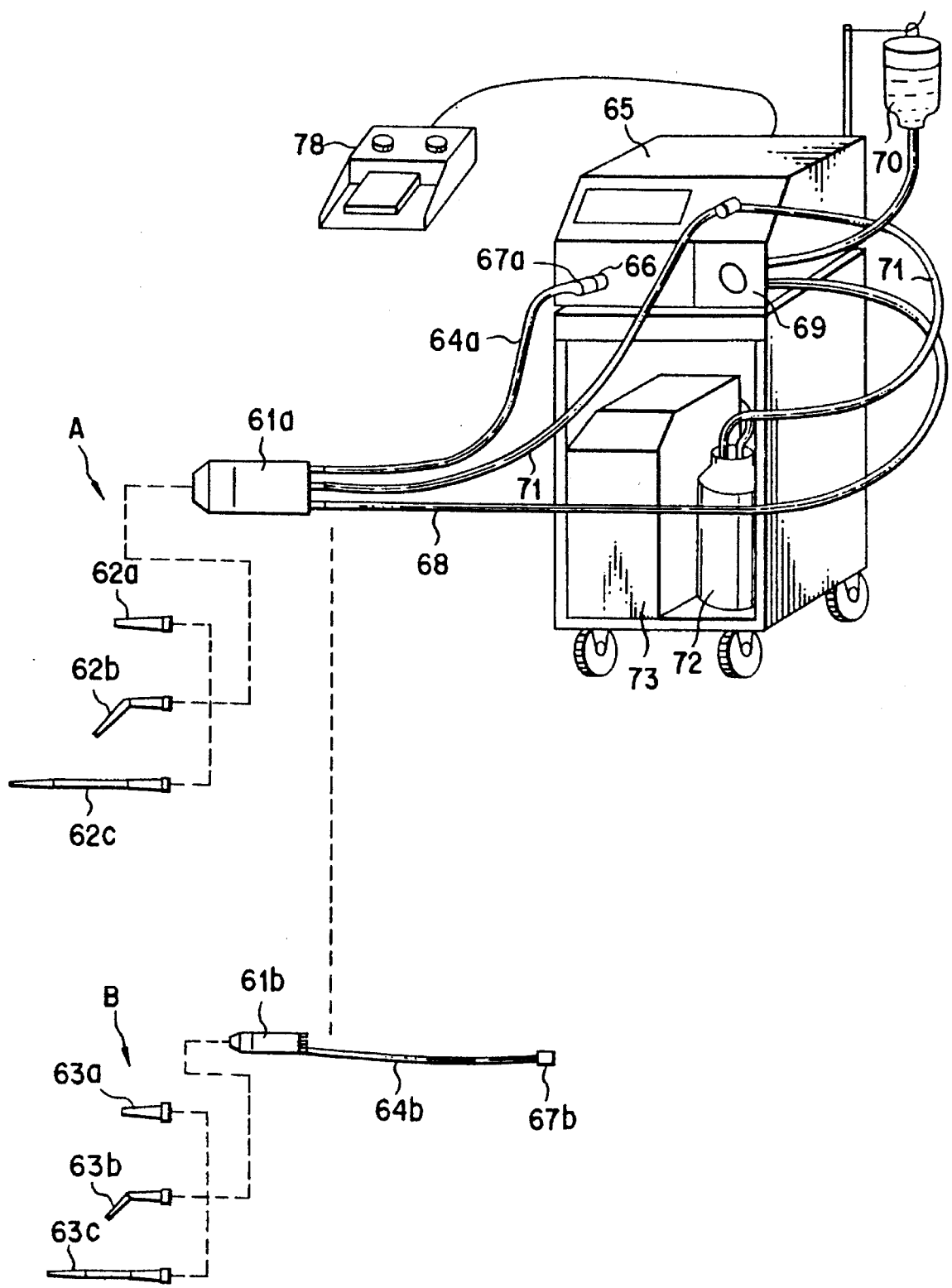
F I G. 11

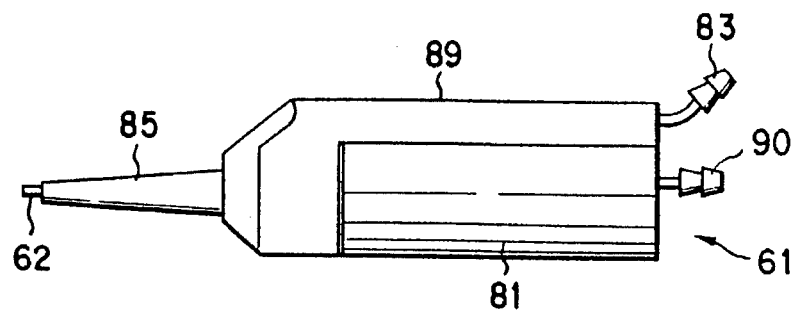
F I G. 15
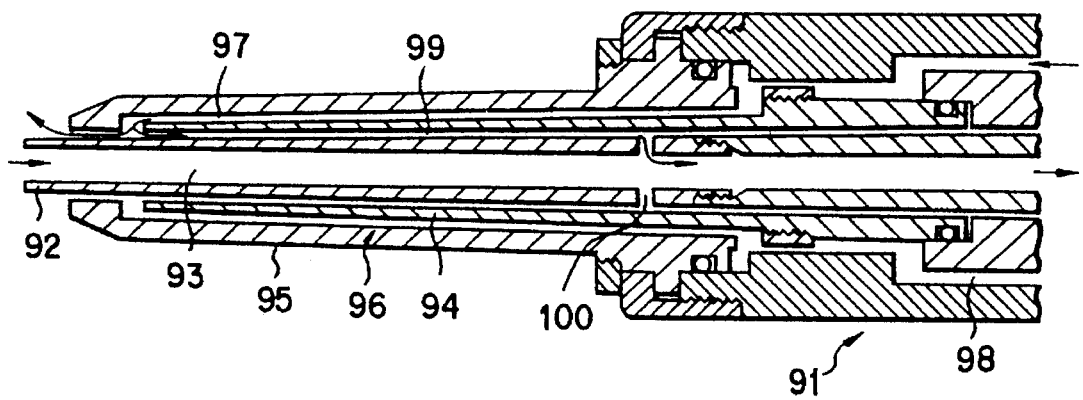
F I G. 16
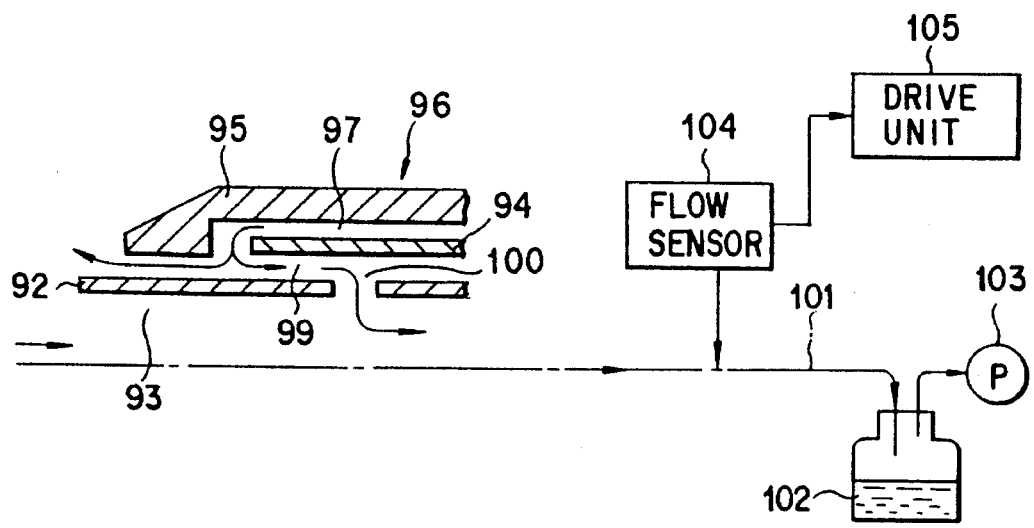
F I G. 17

ULTRASONIC THERAPEUTIC APPARATUS

This is a division of application Ser. No. 08/166,520 filed Dec. 3, 1993 now U.S. Pat. No. 5,462,522 issued 10/31/95.

BACKGROUND OF THE INVENTION

1. Field of the Invention

The present invention relates to an ultrasonic therapeutic apparatus in which the distal end of a probe is subjected to ultrasonic vibration, thereby crushing or emulsifying organic tissues, and operations for cooling water supply and suction are performed.

2. Description of the Related Art

A typical ultrasonic therapeutic apparatus comprises a hand piece having an ultrasonic vibrator therein, a probe connected to the hand piece, and a drive source unit for driving the vibrator. Since the probe is heated by internal strain which is attributable to ultrasonic vibration, the ultrasonic therapeutic apparatus is furnished with a water supply mechanism which supplies the probe with cooling water, such as a physiological saline solution, thereby cooling the probe and washing the operation field. The apparatus is further provided with a suction mechanism for removing tissue pieces or crushed pieces, along with the supplied cooling water, by suction.

The ultrasonic therapeutic apparatus with this construction can crush organic tissues and successively remove crushed tissue pieces by suction, by subjecting the distal end of the probe to ultrasonic vibration. This apparatus is characterized, however, in that it never crushes elastic tissues, such as vascular tissues, nervous tissues, etc., so that it is suited for resection of the liver and cerebral surgery.

Among specific examples of the ultrasonic therapeutic apparatus of this type, there is one which is provided with a mechanism capable of freely adjusting the quantity of cooling water supply to the probe. Another example is proposed in Jpn. Pat. Appln. Publication No. 3-318867 (Jpn. Pat. Appln. KOKAI Publication No. 5-168897). In this case, the apparatus is driven after preset values for an ultrasonic output and a feedwater output for cooling water are set by reading preset values stored in an internal memory for the preceding cycle of operation.

According to the former ultrasonic therapeutic apparatus in which the quantity of cooling water supply can be freely set, an operator must take the greatest care not to carry out a surgical operation with the cooling water supply at its minimum value or zero. If a preset value for the cooling water supply is changed in the ultrasonic therapeutic apparatus of this type, the probe may not be able to be fully cooled because the quantity of cooling water supply is too small for the ultrasonic output, or the operation field cannot be washed clean enough to secure a distinct field of view. In such a case, the use of the apparatus must be suspended.

The latter ultrasonic therapeutic apparatus proposed in Jpn. Pat. Appln. Publication No. 3-318867 involves the same problem of the former one unless the preset feedwater output value for the preceding operation cycle, invoked from the memory during the operation of the apparatus, is appropriate to the ultrasonic output.

Thus, in the ultrasonic therapeutic apparatus, the water supply to the probe is an essential factor, and the probe should never fail to be properly supplied with water before ultrasonic oscillation. If the water supply is stopped during the ultrasonic oscillation, moreover, the ultrasonic oscillation must be suspended in order to avoid the aforementioned awkward situation.

Depending on the application, the conventional ultrasonic therapeutic apparatus requires the provision of hand pieces and probes with different shapes, sizes, outputs, etc. For example, there are many types of hand pieces, including a bent type for cerebral surgery, standard type for general surgical operation, high-power type for orthopedic or endoscopic treatment, etc. Also, the probes are varied in distal end shape and length, and some of them have a bent portion. It is poor economy, however, to provide many ultrasonic therapeutic apparatuses for individual applications, and storing them is a hard task.

To cope with this, a novel system is proposed in Jpn. Pat. Appln. Publication No. 2-283322 (Jpn. Pat. Appln. KOKAI Publication No. 4-158856. According to this system, a plurality of combinations of hand pieces and probes can be freely selected according to the application, the selected combination is detected or discriminated, and drive conditions are set in accordance with the combination. To attain this, each hand piece is discriminated by identification means attached to its connector, and the type of the probe is identified by detecting impedance by means of a control section in a drive unit. This system eliminates the aforesaid conventional drawback that an ultrasonic therapeutic apparatus must be provided for each application, and has an advantage in being able to be driven by means of a common drive unit despite the change of the combination of the hand piece and the probe.

Also in this system, the water supply to the probe is essential in washing the operation field or preventing the probe from being heated or damaged. It is necessary, therefore, to detect or discriminate the types of the hand piece and the probe and secure the optimum drive conditions for the combination of the two elements, and also, to set optimum conditions for a water supply pump, thereby adjusting the quantity of water supply to an optimum value corresponding to the ultrasonic oscillation output. Naturally, the drive conditions, including the oscillation output of ultrasonic vibration, in particular, are often expected to be changed depending on the varied tissues, despite the use of the same hand piece and probe. In some surgical operation, the tissues to be treated may cover various regions including adipose tissue, parenchyma of the liver, ambient regions of lymph nodes and blood vessels, and the like. In this case, an optimum oscillation output must be set for each of the tissues.

According to the system proposed in Jpn. Pat. Appln. Publication No. 2-283322, however, preset values for the oscillation output and the quantity of water supply must be changed independently by manual operation. If the quantity of water supply is too small for the oscillation output, therefore, the probe may possibly be heated to be damaged or cause a patient or operator to suffer a burn. If the water supply is too much for the oscillation output, on the other hand, plenty of water flows out from the distal end of the probe into the operation field. As a result, the operation field cannot be clear enough to advance the operation, and the feedwater is inevitably wasted.

SUMMARY OF THE INVENTION

A first object of the present invention is to provide an ultrasonic therapeutic apparatus, in which a preset feedwater output value is secured to prevent a probe from being excessively heated during use, thereby enabling optimum-state use, and which can be operated easily and securely.

A second object of the invention is to provide an ultrasonic therapeutic apparatus of high safety performance, in which a common drive unit can be used in combination with various hand pieces and probes, depending on the kinds and conditions of surgical operations, and the probes can be prevented from being excessively heated or damaged even though preset output values are changed.

These objects of the present invention are achieved by an ultrasonic therapeutic apparatus constructed as follows. The apparatus comprises an apparatus body including a drive source for ultrasonic oscillation, a hand piece including an ultrasonic vibrator and removably connected to the apparatus body, drive means in the apparatus body for applying voltage to the ultrasonic vibrator of the hand piece, thereby driving the ultrasonic vibrator, a probe removably connected to the hand piece and adapted to be vibrated by ultrasonic vibration produced as the ultrasonic vibrator is driven, thereby treating organic tissue, water supply means for supplying cooling water to the probe, suction means for removing waste matter by suction from the organic tissue treated by means of the cooling water and the probe, ultrasonic output setting means for setting a preset value for an ultrasonic output from the ultrasonic vibrator, feedwater output setting means for setting a preset value for a feedwater output from the water supply means, feedwater output control means for controlling the feedwater output setting by the feedwater output setting means so that the preset feedwater output value is a value such that the probe is not excessively heated, and memory means for storing the preset values for the ultrasonic output and the feedwater output.

The feedwater output control means includes recommended value determining means for determining a recommended value for the feedwater output in accordance with the preset value set by the ultrasonic output setting means, and first comparing and setting means for comparing the recommended value and the feedwater output value stored in the memory means and setting a greater one of the compared values as the preset feedwater output value.

In another aspect of the invention, the feedwater output control means includes recommended value determining means for determining a recommended value for the feedwater output in accordance with the preset value set by the ultrasonic output setting means, and comparing and setting means for comparing the recommended value and the preset feedwater output value set by the feedwater output setting means and storing the memory means with a greater one of the compared values as the stored feedwater output value.

In still another aspect of the invention, the feedwater output control means includes minimum value determining means for determining a minimum value for the feedwater output in accordance with the preset value set by the ultrasonic output setting means, and second comparing and setting means for comparing the minimum value and the preset value set by the feedwater output setting means and setting a greater one of the compared values as the preset feedwater output value.

In a further aspect of the invention, the apparatus comprises an apparatus body including a drive source for ultrasonic oscillation, a hand piece including an ultra-sonic vibrator and removably connected to the apparatus body, drive means in the apparatus body for applying voltage to the ultrasonic vibrator of the hand piece, thereby driving the ultrasonic vibrator, a probe removably connected to the hand piece and adapted to be vibrated by ultrasonic vibration produced as the ultrasonic vibrator is driven, thereby treating organic tissue, water supply means for supplying cooling water to the probe, suction means for removing waste matter by suction from the organic tissue treated by means of the cooling water and the probe, hand piece detecting means for detecting the type of-the hand piece connected to the apparatus body, probe detecting means for detecting the type of the probe connected to the hand piece, ultrasonic output setting means for setting a preset value for an ultrasonic output from the ultrasonic vibrator in accordance with detection signals from the hand piece detecting means and the probe detecting means, feedwater output setting means for setting a preset value for a feedwater output from the water supply means, feedwater output control means for controlling the feedwater output setting by the feedwater output setting means so that the preset feedwater output value is a value such that the probe is not excessively heated, and memory means for storing the preset values for the ultrasonic output and the feedwater output.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 9 is a flow chart for illustrating the operation of an ultrasonic therapeutic apparatus according to a modification of the third embodiment;

FIG. 11 is a perspective view showing another arrangement of the apparatus of the invention;

FIG. 15 is a schematic view showing a second embodiment of the hand piece to be connected to the apparatus of the invention;

FIG. 16 is a partial sectional view showing a third embodiment of the hand piece to be connected to the apparatus of the invention;

FIG. 17 is a diagram schematically showing an arrangement of a feedwater suction system for the hand piece of FIG. 16.

DETAILED DESCRIPTION OF THE PREFERRED EMBODIMENTS

Figure 1:
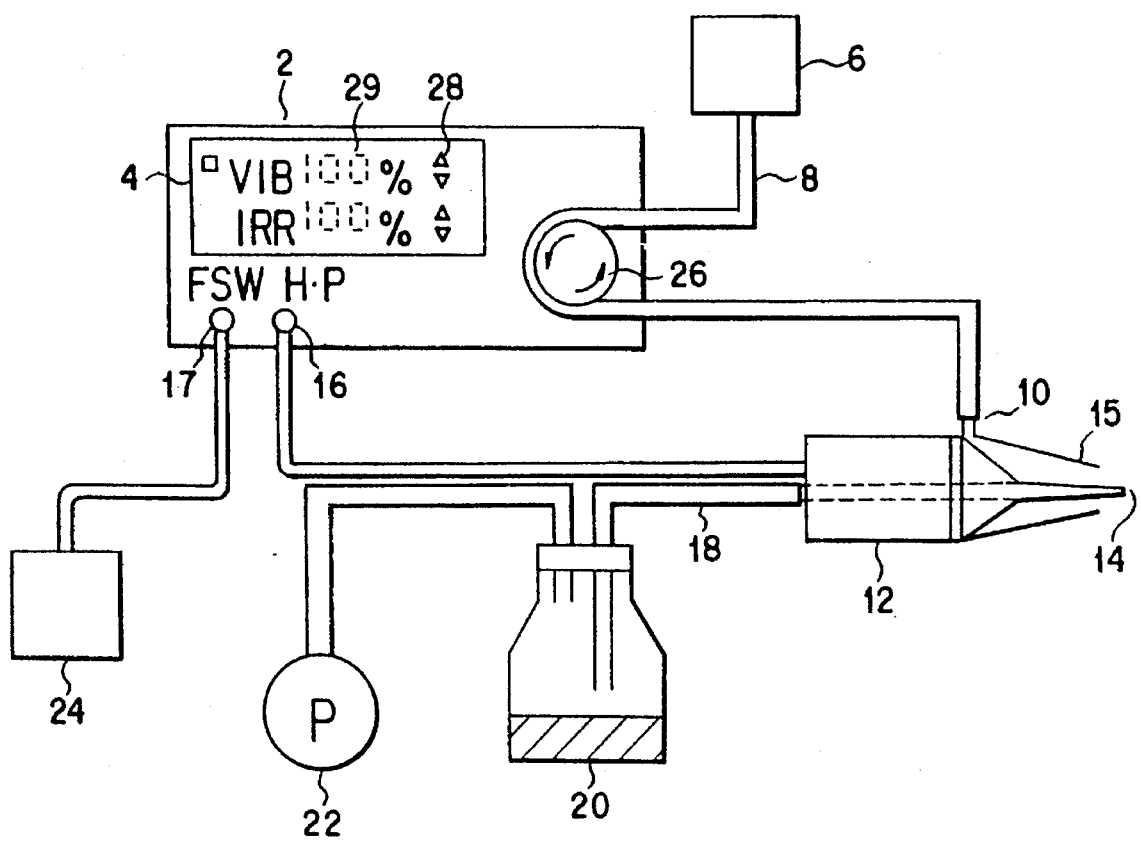
FIG. 1 is a general view schematically showing an ultrasonic therapeutic apparatus according to the present invention.

Preferred embodiments of the present invention will now be described with reference to the accompanying drawings. FIG. 1 schematically shows the system of an ultrasonic therapeutic apparatus according to a first embodiment of the present invention. The ultrasonic therapeutic apparatus comprises an apparatus body 2, which contains therein a control section, driver circuit (not shown), etc. An operation/display panel 4 is arranged on the outer surface of the body 2. The panel 4 is provided with alteration switches 28 for changing preset values of an ultrasonic output and a feedwater output and a display section 29 for displaying these outputs.

A hand piece 12 and a foot switch 24 are removably connected to the apparatus body 2 by means of connectors 16 and 17, respectively. In response to an on-off operation by means of the foot switch 24, the hand piece 12 is driven by the driver circuit.

A probe 14 is removably fastened to the hand piece 12. A sheath 15 is fitted on the probe 14 in a manner such that a passage is defined between the probe 14 and the sheath 15. This passage is connected to a water supply port 10 which is supplied with a physiological saline solution for probe cooling and the like. The port 10 is connected with one end of a water supply tube 8, the other end of which is connected to a water supply tank 6. A roller pump 26 is provided in the middle of the tube 8. These elements constitute water supply means for cooling the probe 14.

A hollow line (not shown) is defined in the hand piece 12 and the probe 14, and a suction tube 18 is connected to the rear end of the hollow line. The tube 18 is connected to a suction pump 22 through a suction bottle 20 for removing sucked substances.

Figure 2:
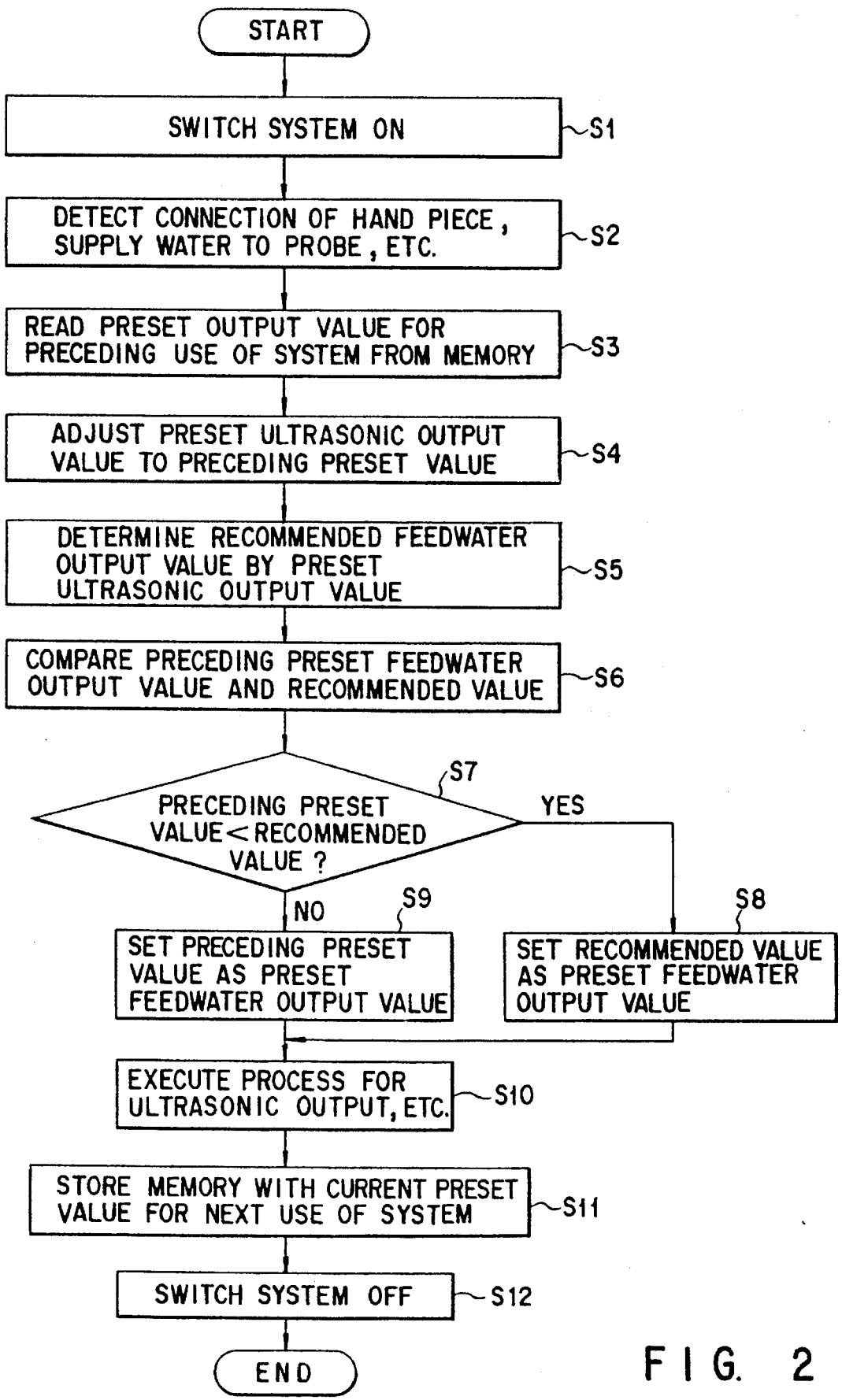
FIG. 2 is a flow chart for illustrating the operation of an ultrasonic therapeutic apparatus according to a first embodiment of the invention.

Referring now to the flow chart of FIG. 2, the operation of the ultrasonic therapeutic apparatus according to the first embodiment will be described.

First, in Step S1, the apparatus is connected to the supply, and the hand piece 12 is connected to the apparatus body 2. Thereupon, the control section in the body 2 detects the connection of the hand piece 12, and starts water supply to the probe 14 which is connected to the hand piece 12, in Step $2. When an enabled state for the ultrasonic output is established, the preset output value for the preceding cycle of operation is read from an internal memory in Step S3, and the preset ultrasonic output value is adjusted to the preset output value for the preceding cycle in Step S4.

Figure 4:
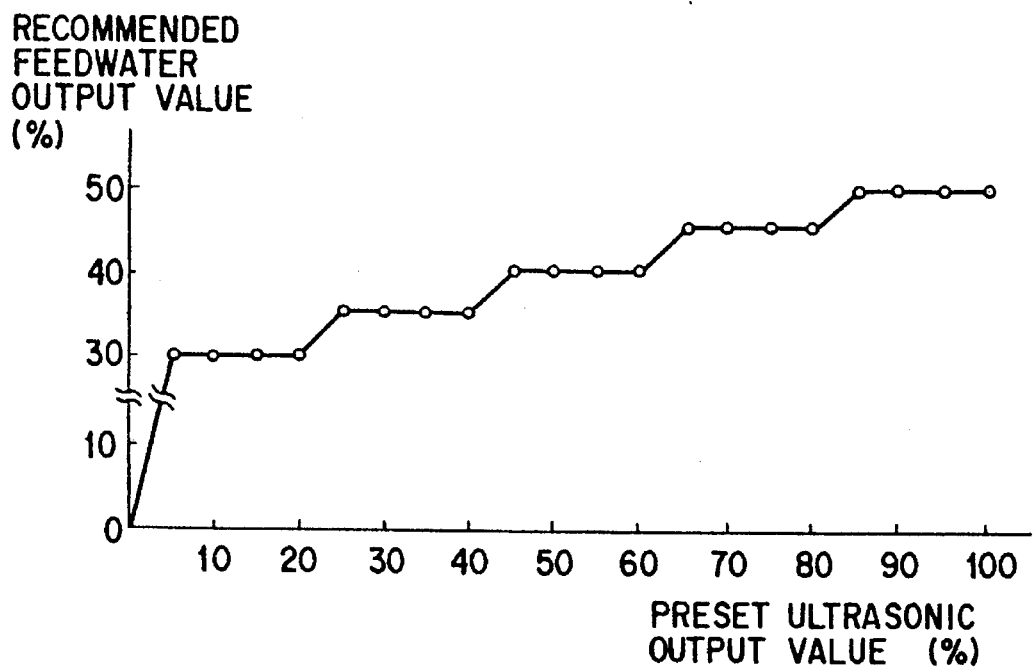
FIG. 4 is a graph showing the recommended feedwater output value compared with the preset ultrasonic output value.

The control section is previously stored, as a recommended feedwater output value, with a preset output value for a feedwater quantity such that the probe is not heated, corresponding to the preset ultrasonic output value in the relation shown in FIG. 4, for example. In Step S5, the recommended feedwater output value is determined in accordance with the read preset ultrasonic output value.

Then, the program proceeds to Steps S6 and S7, whereupon the preceding preset value for the feedwater output previously read from the memory in the control section is compared with the recommended feedwater output value. If the preceding preset value is smaller than the recommended value, the program proceeds to Step S8, whereupon the recommended value is set as the preset feedwater output value. If the preceding preset value is greater than the recommended value, on the other hand, the program proceeds to Step S9, whereupon the preceding preset value is set as the preset feedwater output value. These preset values are displayed on the display section 29 of the operation/display panel 4.

By operating the foot switch 24 in Step S10, thereafter, ultrasonic waves can be outputted for treatment. It is desirable to prohibit ultrasonic treatment using the foot switch 24 unless the feedwater is set.

when the treatment is finished, the aforesaid preset value is stored in the internal memory of the control section to be ready for another cycle of operation of the system in Step S11, and the operation terminates when the power supply is cut off in Step S12.

Thus, according to the present embodiment, the preset feedwater output value with which the probe is not heated corresponding to the preset ultrasonic output value can be ensured at the start of the use of the system. Accordingly, the probe can be prevented from being heated by the use of the small preset feedwater output value at the start of the use of the system, so that breakage of the probe by heat and bad influences on organic tissue can be prevented. Thus, the ultrasonic therapeutic apparatus can! always be used under proper conditions.

Figure 3:
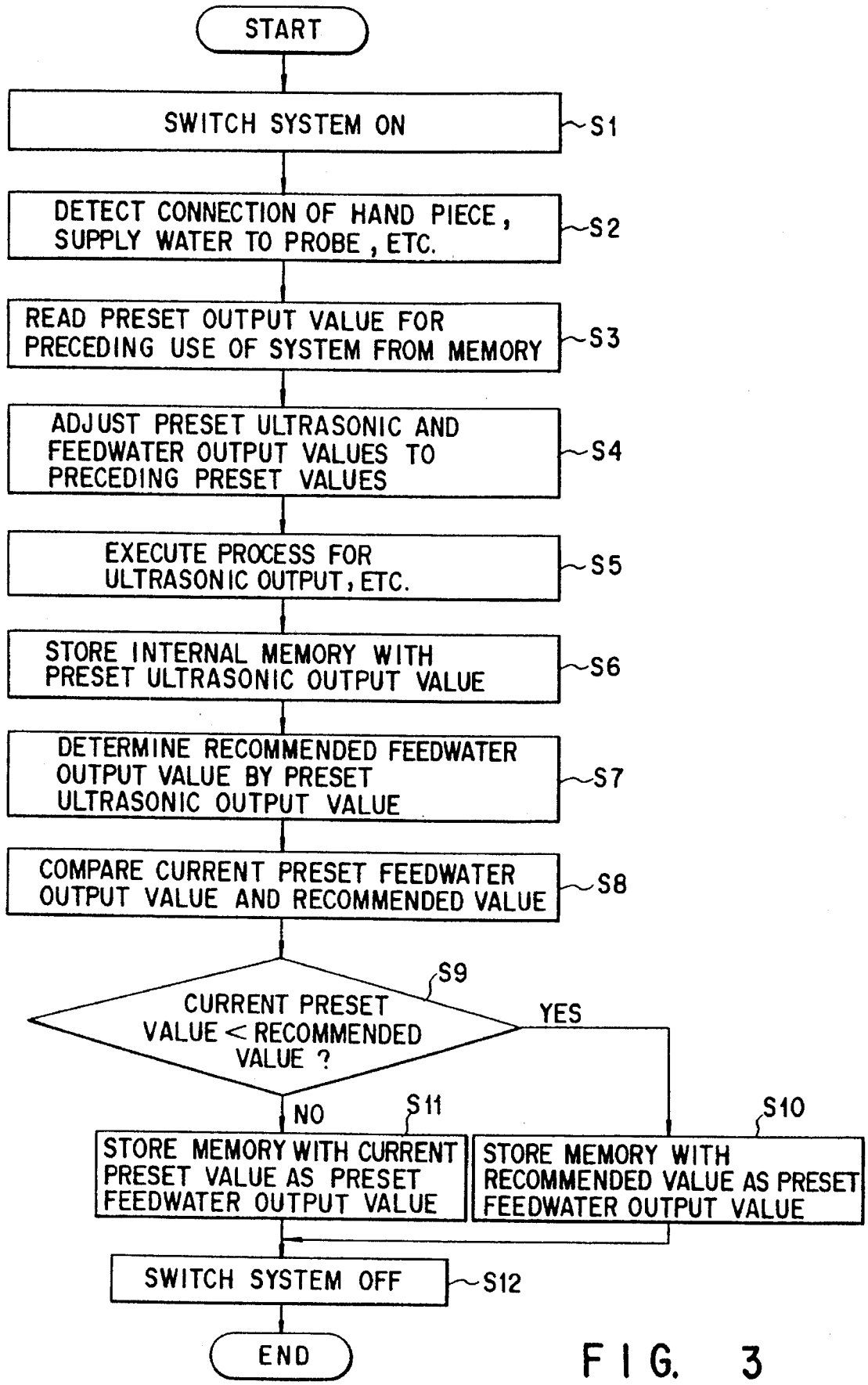
FIG. 3 is a flow chart for illustrating the operation of an ultrasonic therapeutic apparatus according to a modification of the first embodiment.

FIG. 3 shows a modification of the first embodiment described above. In this modification, the feedwater output is set in Step S11 of FIG. 2 in the aforementioned operation according to the first embodiment.

In this case, as shown in FIG. 3, the processes of Steps S1 to S4 are executed in the same manner as in the first embodiment, and ultrasonic waves are outputted for treatment by operating the foot switch 24 in Step S5. In Step S6, thereafter, the preset ultrasonic output value is stored in the internal memory.

Subsequently, the recommended feedwater output value is determined in accordance with the stored preset ultrasonic output value in Step S7, and the program then proceeds to Steps S8 and S9. Thereupon, the current preset feedwater output value used in the previous process for the delivery of the ultrasonic waves or the like is compared with the recommended feedwater output value. If the current preset output value is smaller than the recommended value, the program proceeds to Step S10, whereupon the recommended value is stored as the preset feedwater output value in the memory. If the current preset output value is greater than the recommended value, on the other hand, the program proceeds to Step S11, whereupon the current preset output value is stored as the preset feedwater output value in the memory.

When the preset feedwater output value is stored in the internal memory in this manner, the power supply is cut off so that the operation terminates in Step S12.

Thus, the same effect of the first embodiment can be also obtained by setting the feedwater output in the process of the storage in the internal memory of the control section.

Figure 5:
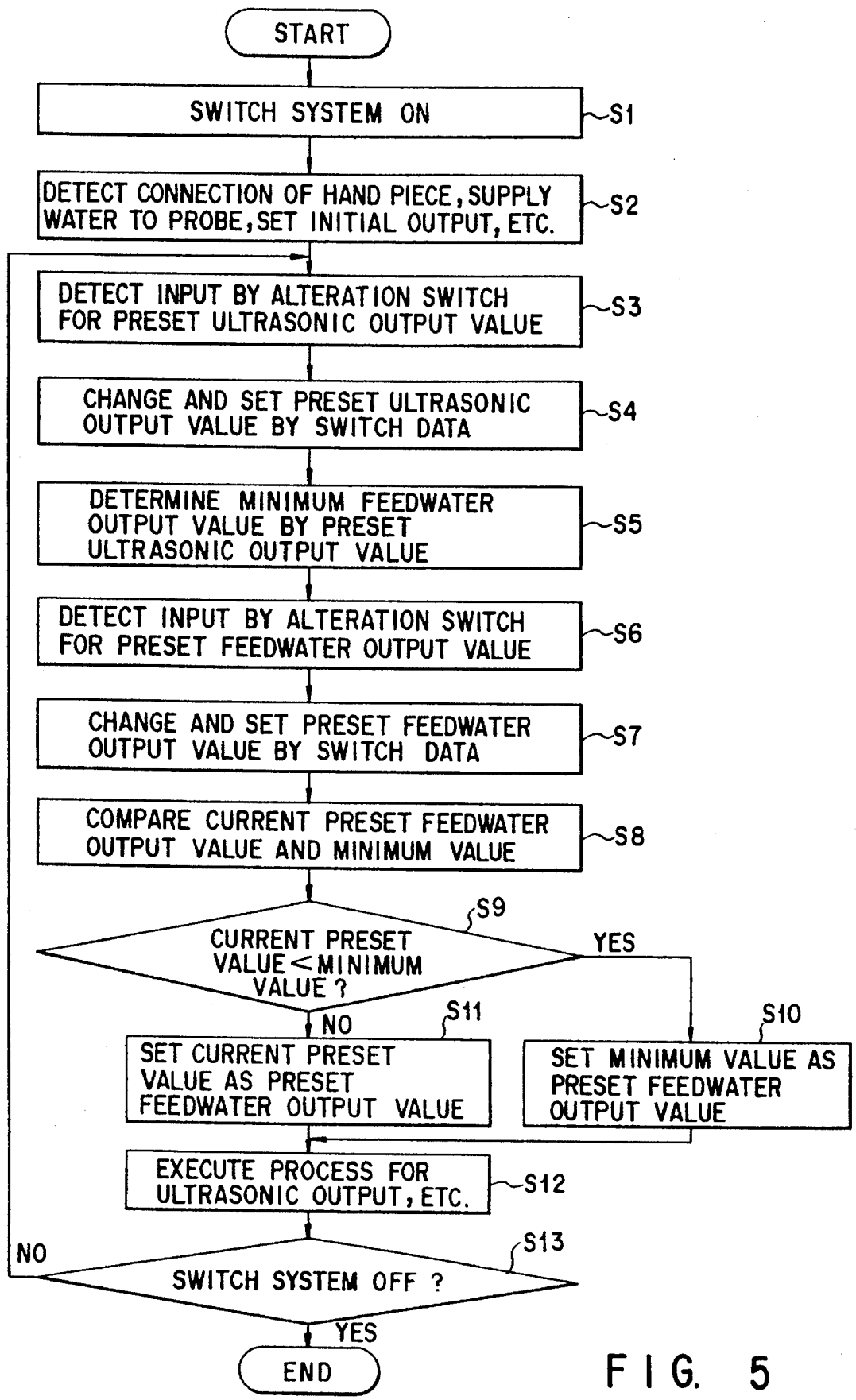
FIG. 5 is a flow chart for illustrating the operation of an ultrasonic therapeutic apparatus according to a second embodiment of the invention.

Referring now to FIG. 5, a second embodiment of the present invention will be described. An ultrasonic therapeutic apparatus according to the present embodiment is constructed in the same manner as the aforementioned apparatus of the first embodiment except for a characteristic program stored in the control section of the apparatus body 2. The following is a description of the operation of this apparatus. First, in Step Sl, the apparatus is connected to the power supply, and the hand piece 12 is connected to the apparatus body 2, as in the case of the first embodiment. In Step S2, the control section detects the connection of the hand piece 12, and starts water supply to the probe 14 which is connected to the hand piece 12. When the enabled state for the ultrasonic output is established, the preset output value for the preceding cycle is read from an internal memory, and the preset ultrasonic and feedwater output values are adjusted to the preset values for the preceding cycle. Ultrasonic waves can be outputted for treatment by operating the foot switch 24 in this state.

In modifying the displayed preset values, an operator operates the preset value alteration switches 28 on the operation/display panel 4.

When the control section detects an input operation by means of the alteration switch 28 for the preset ultrasonic output value in Step S3, the preset ultrasonic output value is modified into a new preset value on the basis of data for the increase or decrease of the preset values.

Figure 6:
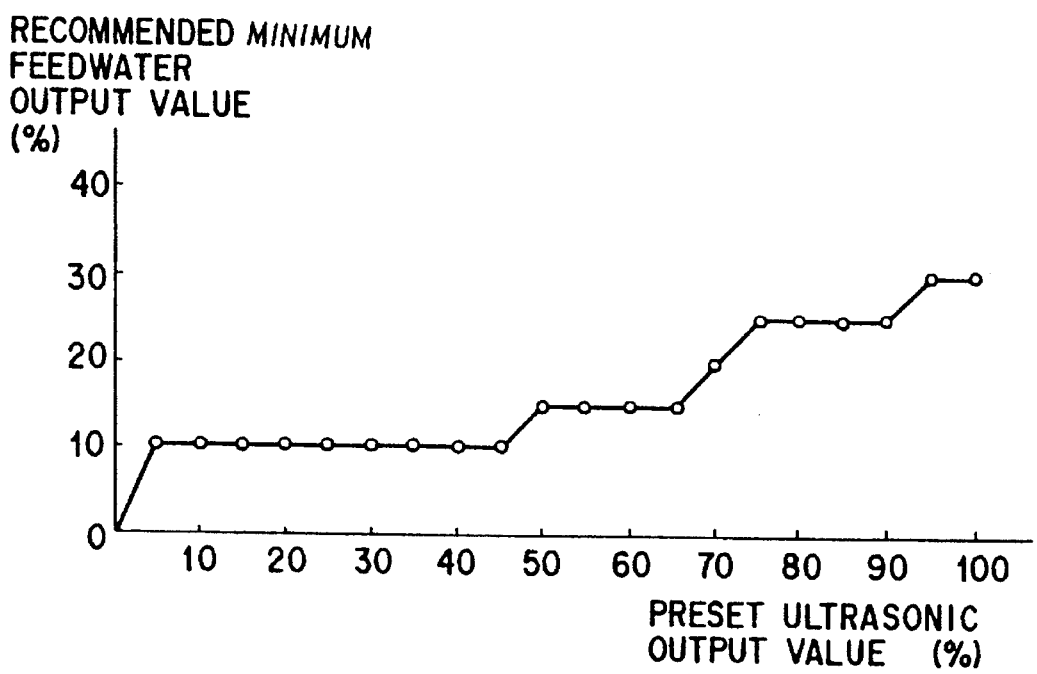
FIG. 6 is a graph showing the minimum feedwater output value compared with the preset ultrasonic output value.

The control section is previously stored, as a minimum feedwater output value, with the preset feedwater output value with which water is supplied corresponding to the preset ultrasonic output value without heating the probe, as shown in FIG. 6, for example. Then, in Step S5, the minimum feedwater output value is determined in accordance with the newly set ultrasonic output value.

When an input operation by means of the alteration switch 28 for the preset feedwater output value is then detected in step S6, the preset feedwater output value is modified and set in the same manner for the ultrasonic output in Step S7.

Thereafter, the program proceeds to Steps S8 and S9, whereupon the newly set feedwater output value and the minimum feedwater output value are compared. If the current preset value is smaller than the minimum value, the program proceeds to Step S10, whereupon the minimum value is set as the preset feedwater output value. If the current preset value is greater than the minimum value, on the other hand, the program proceeds to Step S11, whereupon the current preset value is set as the preset feedwater output value. These preset values are displayed on the display section on 29 of the operation/display panel 4.

In this state, the program proceeds to Step S12, whereupon ultrasonic waves can be outputted for treatment by operating the foot switch 24.

For continuous treatment, the program returns from Step S13 to S3 unless the power supply is cut off, whereupon the treatment is continued. The operation terminates when the power supply is cut off.

Thus, according to the present embodiment, the preset feedwater output value with which the probe is not heated corresponding to the preset ultrasonic output value can be ensured during the use of the system. Accordingly, the probe can be prevented from being heated by the use of the small preset feedwater output value during the use of the system. Thus, the ultrasonic therapeutic apparatus can always be used under proper conditions.

Figure 7:
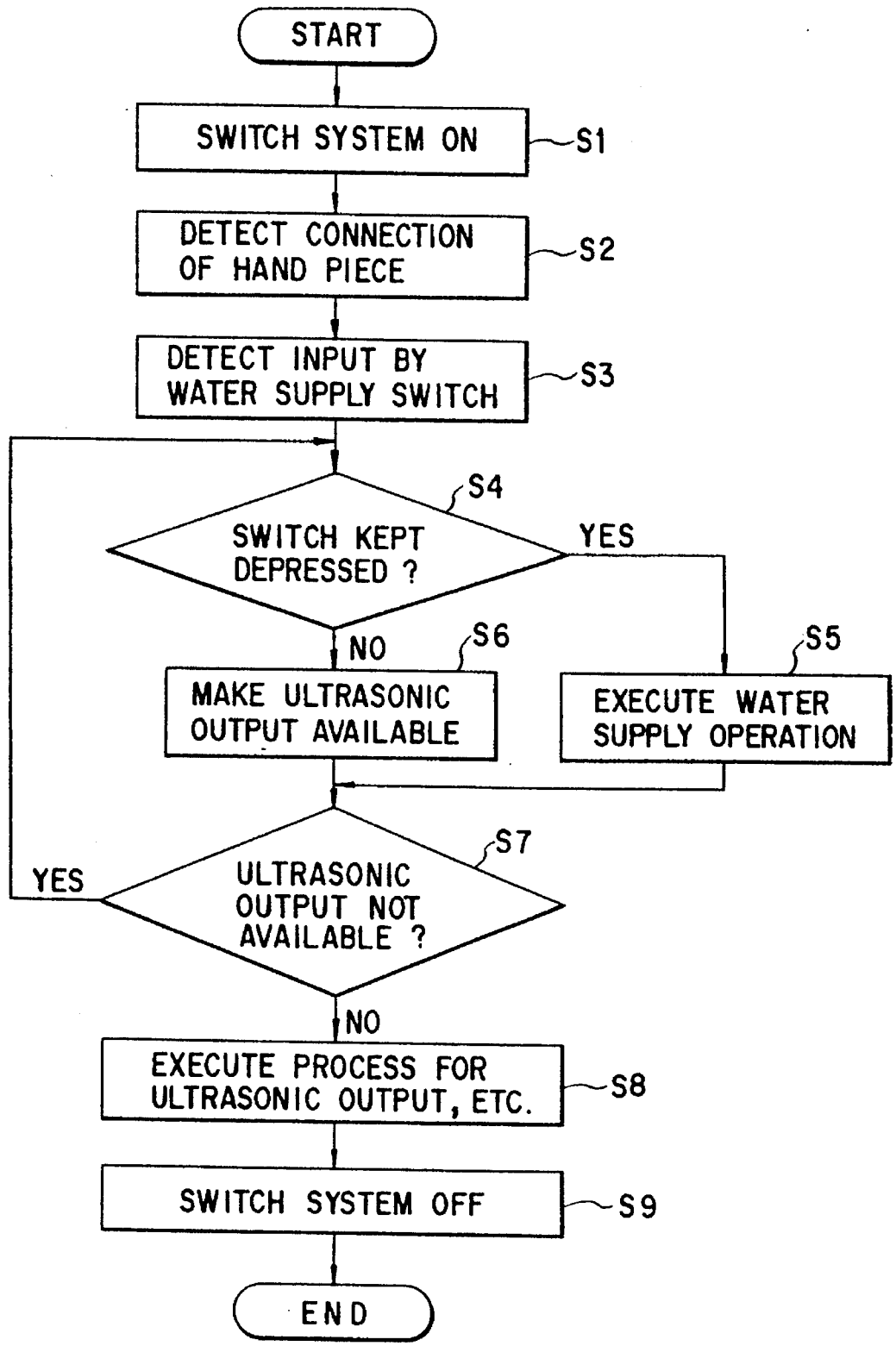
FIG. 7 is a flow chart showing a flow chart for illustrating a preferred embodiment of water supply operation of the apparatus of the invention.

Referring now to FIG. 7, a method for ensuring safety in starting the use of the ultrasonic therapeutic apparatus will be described.

Conventionally, the ultrasonic therapeutic apparatus is brought to the enabled state for the ultrasonic output by only inputting a detection signal for the connection of the hand piece 12 after connecting the system to the power supply. Accordingly, cooling water is not fed to the probe 14 on the hand piece 12 in the enabled state for the ultrasonic output during the initialization of the system. If ultrasonic waves are outputted in this state, therefore, the probe 14 may possibly be damaged by heat. This apparatus is improved in this regard. 10 First, in Step Sl, the apparatus, which is constructed in the same manner as the apparatus of the first embodiment, is connected to the power supply. When the hand piece 12 is then connected to the apparatus body 2, the control section detects the connection of the hand piece 12 in Step S2. Thereafter, the apparatus body 2 is brought to a standby state for water supply to the probe 14 which is connected to the hand piece 12. In this state, an instruction for the operator's water supply operation is displayed on the display section 29 of the operation/display panel 4.

When the operator then operates the foot switch 24 or a water supply switch on the operation/display panel 4 in Step S3, a signal indicative of the switch operation is detected.

When the depression of the switch is continued, the program proceeds to Step S5, whereupon the water supply operation is performed. When the switch is released, the program proceeds to Step S6, whereupon the water supply operation is completed, and the enabled state for the ultrasonic output is established. In this state, the preset output value for the preceding cycle is read from the internal memory, set, and displayed. If it is concluded in Step S7 that the water supply is not accomplished and that the enabled state for the ultrasonic output is not established, the program returns to Step S4, whereupon the aforesaid processes are repeated so that the water supply operation is completed.

By operating the foot switch 24 in Step S8, thereafter, ultrasonic waves can be outputted for treatment.

With the ultrasonic therapeutic apparatus constructed in this manner, the operator must necessarily perform the water supply operation for a suitable period of time before the enabled stake for the ultrasonic output is established, after the connection of the hand piece is detected at the start of the use of the system. Thus, the apparatus can be used under safe conditions.

Even in case only the hand piece 12 is replaced during use, moreover, the water supply operation can be easily performed for a period of time during which the switch is depressed. Thus, troublesome preparations are not required before starting the system operation.

Figure 8:
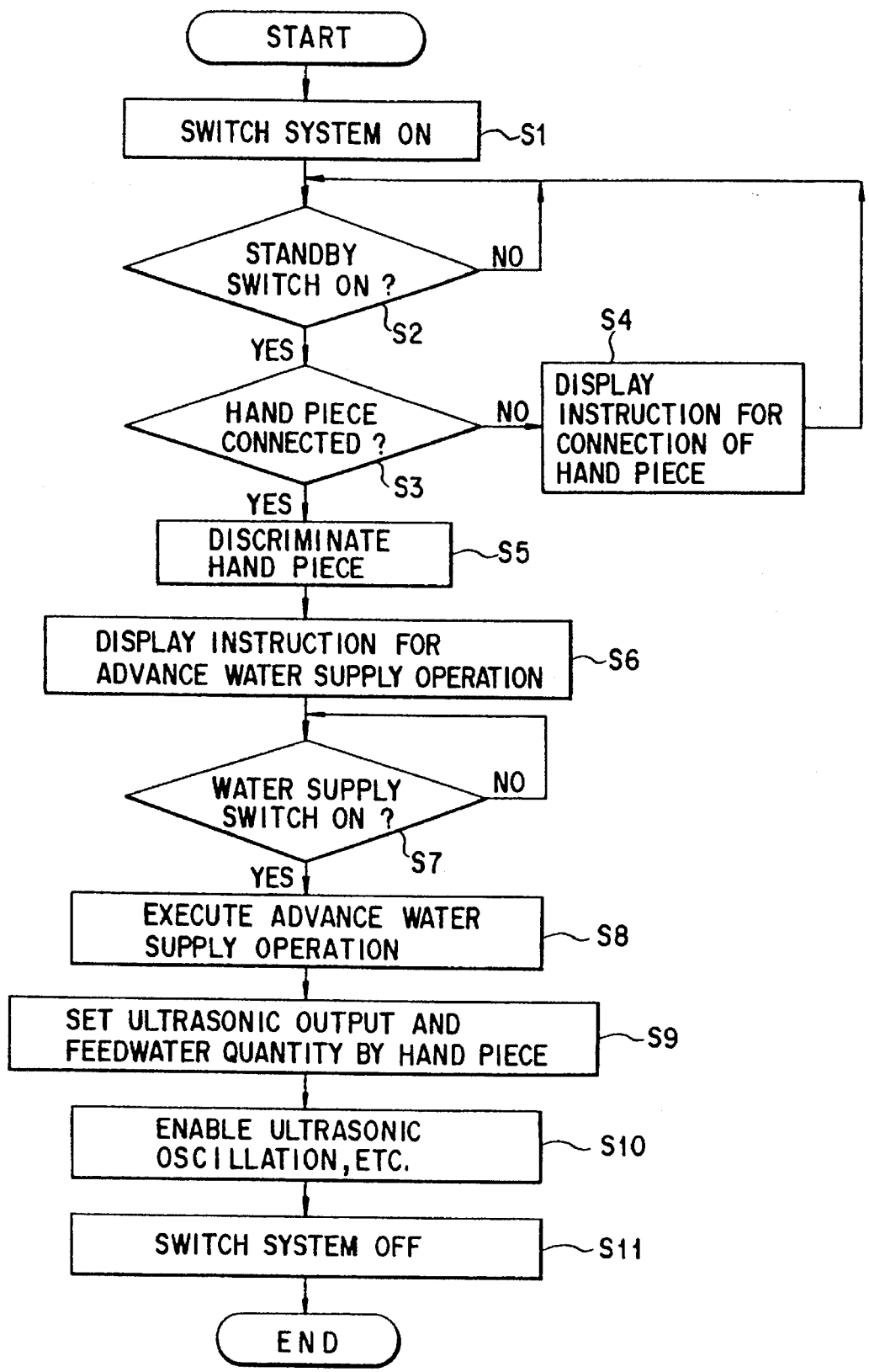
FIG. 8 is a flow chart for illustrating the operation of an ultrasonic therapeutic apparatus according to a third embodiment of the invention.

Referring now to FIG. 8, a third embodiment of the present invention will be described. An ultrasonic therapeutic apparatus according to the present embodiment is constructed in the same manner as the aforementioned apparatus of the first embodiment, provided that a plurality of types of hand pieces 12 can be connected to the apparatus. The operation of this apparatus will be described with reference to the flow chart of FIG. 8.

After the system is first connected to the power supply in Step Sl, a standby switch is depressed. In response to the operation of the standby switch in Step S2, the presence of the hand piece 12 to be connected is detected in Step S3. If it is concluded that the hand piece 12 is not connected, an instruction for the connection of the hand piece 12 is displayed in Step S4. If the hand piece 12 is connected, its type is discriminated in Step S5. The result of decision in Step S5 is used in setting the ultrasonic output and feedwater output afterward.

In Step S6, thereafter, an instruction for an advance water supply operation is displayed. The water supply switch is operated in Step S7, and the advance water supply operation is performed in Step S8. Water is supplied up to the distal end of the hand piece 12. In Step S9 after the advance water supply is completed, the previously discriminated data for the hand piece 12 is invoked from a preset data table for the ultrasonic waves and feedwater quantity. By doing this, operations for ultrasonic oscillation, washing, and suction are allowed to be started by means of the foot switch (Step S10). The operation terminates when the power supply is cut off.

The flow may be arranged so that the standby switch and the water supply switch are common. As shown in FIG. 9, moreover, the operation of the standby switch may be omitted so that the hand piece 12 is discriminated as its connection is detected.

According to the this embodiment, automatic setting of the recommended feedwater quantity corresponding to the ultrasonic output, which constitutes a feature of the present invention, may be applied to an apparatus body which can be used with various types of hand pieces 12.

As shown in FIG. 9, moreover, the present embodiment may be designed so that the advance water supply operation for the ultrasonic oscillation can be controlled by means of the operator-operated foot switch (Step S7) as well as the standby switch attached to the apparatus body 2 (Step S6). If neither of the switches is turned on, an instruction for the advance water supply operation is displayed in Step S6. Thus, the operator can successfully set up the apparatus without failing to touch the apparatus body 2 in a foul region.

Figure 10:
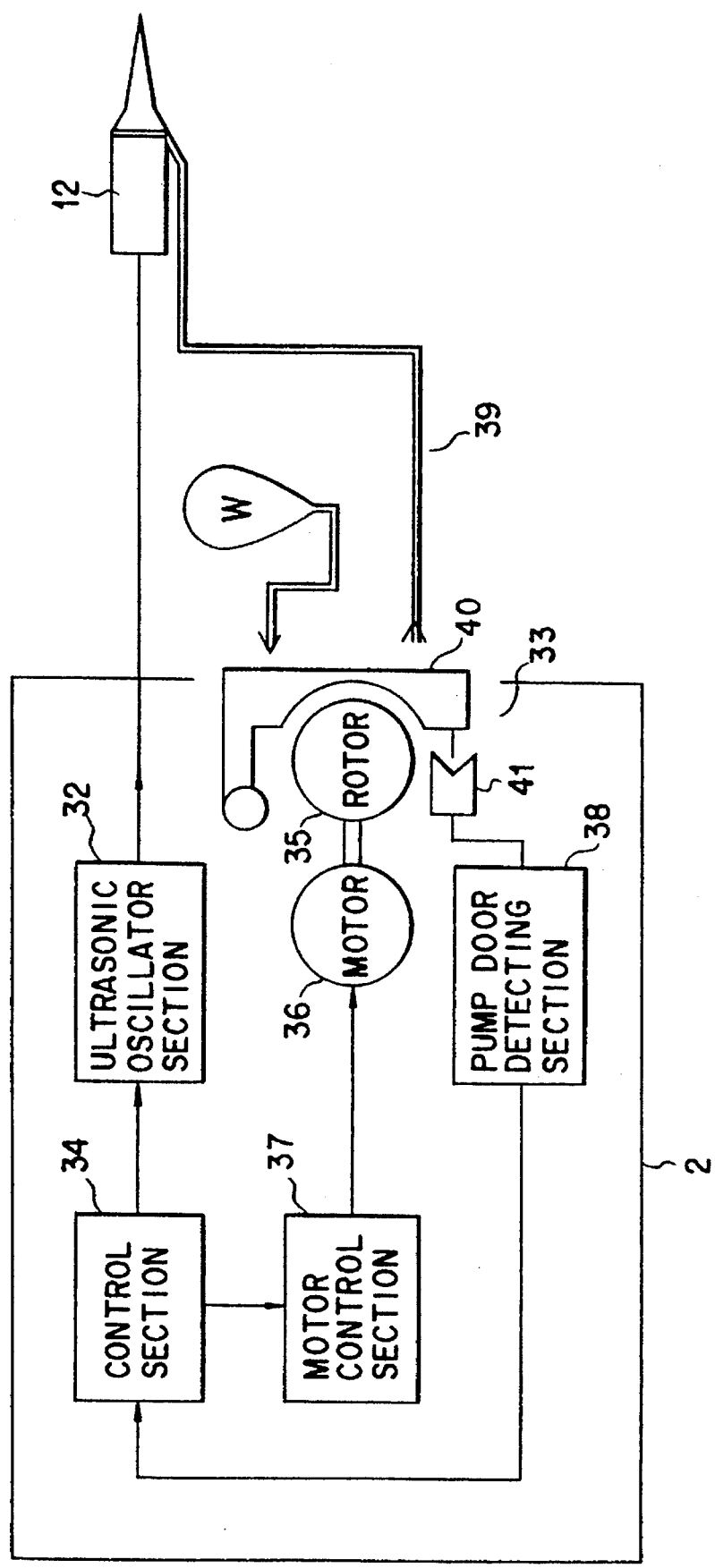
FIG. 10 is a schematic view showing a preferred embodiment of a water supply mechanism of the apparatus of the invention.

Referring now to FIG. 10, a preferred embodiment of a water supply mechanism of the ultrasonic therapeutic apparatus according to the present invention will be described. The apparatus body 2 is provided with an ultrasonic oscillator section 32, a water supply section 33, and a control section 34. Also, the hand piece 12 is connected to the body 2. The water supply section 33 comprises a rotor 35, a motor 36, a motor control section 37, and a pump door detecting section 38. The rotor 36 is fitted with a tube 39. As the rotor 36 is rotated, the tube 39 is squeezed so that water is supplied. The pump door 40 serves to cover the rotating rotor 35 and presses the tube 39 against the rotor 35. The water supply cannot be normal unless the door 40 is fully closed. If unsatisfactory closing of the pump door 40 is detected by means of a sensor 41 for detecting the door state, therefore, the advance water supply operation or ultrasonic oscillation is prohibited. Also, the operator may be informed of this situation by being warned.

According to the present embodiment, the ultrasonic oscillation cannot be continued when the water supply mechanism ceases to perform satisfactory water supply operation after the advance water supply and ultrasonic oscillation are effected.

Thus, in the ultrasonic therapeutic apparatuses according to the individual embodiments described above, the feedwater output value is set corresponding to the preset ultrasonic output value of ultrasonic vibrators, and the probe can be restrained from being heated. Accordingly, ultrasonic waves cannot be delivered with a relatively low feedwater output at the start of or during the use of the apparatus, and so that appropriate water supply operation corresponding to the preset ultrasonic output value can be carried out before the ultrasonic oscillation, and the apparatus can be used under good conditions. Furthermore, recommended feedwater values suited for a plurality of hand pieces can be set, and lower limit values for modified setting can be determined in accordance with the recommended values.

FIG. 11 shows another arrangement of the ultrasonic therapeutic apparatus according to the present invention.

FIG. 11, numerals 61a and 61b denote hand pieces, which are different in size, maximum amplitude, frequency, etc. The hand piece 61a is adapted to be fitted with probes 62a, 62b and 62c which are different in shape, size, etc. The hand piece 61b is adapted to be fitted with probes 63a, 63b and 63c which are different in shape, size, etc. The probes 62a, 62b, 62c, 63a, 63b and 63c can be removably mounted in various combinations on the hand pieces 61a and 61b. In this case, the combinations of the hand pieces and the probes are classified into two groups, Group A including the hand piece 61a and the probes 62a, 62b and 62c and Group B including the hand piece 61b and the probes 63a, 63b and 63c.

Cords 64a and 64b extend from the hand pieces 61a and 61b, respectively, and connectors 67a and 67b to be connected to a connector socket 66 of a drive unit 65 are attached to the extreme ends of the cords 64a and 64b, respectively.

Detecting means are provided for individually discriminating the types of the hand pieces 61a and 61b, which have different drive characteristics, and the probes 62a, 62b, 62c, 63a, 63b and 63c. Arranged individually in the connectors 67a and 67b are discrimination elements (not shown), such as resistors, Zener diodes, etc., for use as means for detecting the types of the hand pieces 61a and 61b. If the discrimination elements are resistors, their resistances are changed according to the types of the hand pieces 61a and 61b. If the zener diodes are used, their Zener voltage values are changed according to the types of the hand pieces.

In either case, discrimination terminals, which are connected electrically with the discrimination elements, project individually from the connectors 67a and 67b, and are connected to detecting contacts (not shown) attached to the connector-socket 66 of the drive unit 65.

Further, the drive unit 65 contains detecting means (not shown) for discriminating the type of the combination of the hand piece 61a or 61b and the probe 62a, 62b, 62c, 63a, 63b or 63c. These detecting means discriminate the types of the probes 62a, 62b, 62c, 63a, 63b and 63c by taking advantage of the difference between the voltage or current values for the ultrasonic vibration drive of the hand pieces 61a and 61b fitted with the probes 62a to 63c. More specifically, the detecting means discriminate the types of the probes 62a to 63c by detecting an impedance value (Z) given by a voltage-to-current ratio (V/I), for example.

These detecting means are used to discriminate the types of the hand pieces 61a and 61b and those of the probes 62a, 62b, 62c, 63a, 63b and 63c. Based on the results of discrimination, the drive unit 65 is set under optimum conditions according to the type of the combination of the hand piece 61a or 61b and the probe 62a, 62b, 62c, 63a, 63b or 63c.

Formed in each of the hand pieces 61a and 61b is a passage (not shown) through which a perfusate is supplied.

The perfusate is used to wash the operation field or cool the ultrasonic vibrator in each hand piece 61a or 61b and the probe 62a, 62b, 62c, 63a, 63b or 63c. The passage is connected to a feedwater pump 69 in the drive unit 65 by means of a water supply tube 68. The feedwater pump 69 feeds a physiological saline solution, for use as the perfusate, stored in a feed-water bottle 70, into the perfusate supply passage of the hand piece 61a or 61b, thereby cooling the hand piece and the probe. The perfusate in the probe 62a, 62b, 62c, 63a, 63b or 63c is supplied through a passage formed in the probe or a passage formed of a gap between the probe and a sheath (not shown) surrounding the probe.

Figure 12:
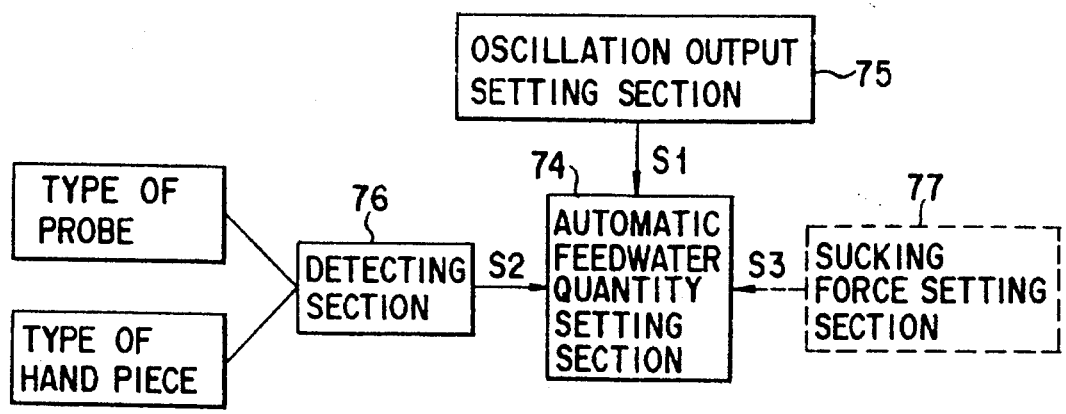
FIG. 12 is a block diagram conceptually showing a detection control system of the apparatus of FIG. 11.

Formed individually in each of the hand pieces 61a and 61b and each of the probes 62a, 62b, 62c, 63a, 63b and 63c, moreover, are suction passages (not shown) for the perfusate through which the perfusate is sucked in after having been used to wash the operation field. These passages are connected to a suction pump 73 in the drive unit 65 by means of a suction tube 71 and a suction bottle 72. The perfusate is supplied and discharged through these passages.

while the perfusate is supplied to the hand piece 61a or 61b by means of the water supply tube 68 and the feedwater pump 69 in the drive unit 65, the necessary quantity of feedwater varies depending on the types of the hand piece 61a or 61b and the probe 62a, 62b, 62c, 63a, 63b or 63c. Accordingly, an initial feedwater value is automatically set as one of optimum drive conditions corresponding to the type of the discriminated hand piece and probe, by means of an automatic feedwater quantity setting section 74 (see FIG. 12).

A surgical operation is started under this preset condition. During the operation, the oscillation output for ultrasonic vibration is suitably set by means of an oscillation output setting section 75 attached to the drive unit 65, depending on the tissue to be operated. If the oscillation output or the amplitude of the ultrasonic vibration is high or large, in this case, heat produced by the ultrasonic vibrator and the probe 62a, 62b, 62c, 63a, 63b or 63c is great, so that the necessary quantity of feedwater is large. If the oscillation output or the amplitude is low or small, on the other hand, the produced heat is small, so that only a small quantity of feedwater is needed.

Since the necessary quantity of feedwater thus varies depending on the preset oscillation output value, the automatic feedwater quantity setting section 74, which is attached to the drive unit 65, automatically sets an optimum feedwater quantity corresponding to the preset oscillation output value in response to a signal. $S_2$ from a detecting section 76 and a signal $S_1$ from the oscillation output setting section 75.

According to this arrangement, the optimum feedwater quantity is automatically set in accordance with the oscillation output, so that the ultrasonic vibrator, probe, etc. can be securely prevented from being heated or damaged even with the oscillation output varied.

The optimum feedwater quantity may be set in the processes of operation previously shown in the flow charts. In this case, the oscillation output setting section 75 sets a proper preset value in response to the signal $S_2$ from the detecting section 76. In response to the signal $S_1$ which depends on the preset value, the automatic feedwater quantity setting section 74 automatically sets the optimum feedwater quantity.

The supplied perfusate is sucked into the suction bottle 72 for recovery through the inside of the probe 62a, 62b, 62c, 63a, 63b or 63c, the suction passage in the hand piece 61a or 61b, and the suction tube 71, by the agency of the suction pump 73. The quantity of the recovered perfusate varies depending on a preset value (sucking force) for the suction pump 73. Accordingly, it is advisable to supply the automatic feedwater quantity setting section 74 with information $S_3$ on the preset sucking force value set by means of a suction force setting section 77 so that the feedwater quantity can be automatically set in consideration of the sucking force. In FIG. 11, numeral 78 denotes a foot switch for the on-off control of the oscillation operation.

According to the arrangement described above, the feedwater quantity is always automatically adjusted to the preset optimum value in accordance with the oscillation output, depending on the types of the detected hand piece 61a or 61b and probe 62a, 62b, 62c, 63a, 63b or 63c or despite the change of the oscillation output. Accordingly, the ultrasonic vibrator in the hand piece and the probe can be prevented from being excessively heated, so that optimum cooling can be effected with reliability. Thus, there is no possibility of a patient or operator suffering a burn, and the ultrasonic vibrator and the probe can be prevented from being damaged by heat. Moreover, a good operation field can always be secured without being obstructed by the feedwater, so that the surgical operation can be carried out smoothly. Furthermore, the feedwater quantity can be adjusted so that the perfusate can be used without waste, thus, ensuring high economical efficiency.

Also, the feedwater quantity can be automatically set in consideration of the sucking force by supplying the automatic feedwater quantity setting section 74 with the information $S_3$ on the preset sucking force value set by means of the suction force setting section 77. Thus, the feedwater quantity can be adjusted with higher accuracy.

Figure 13:
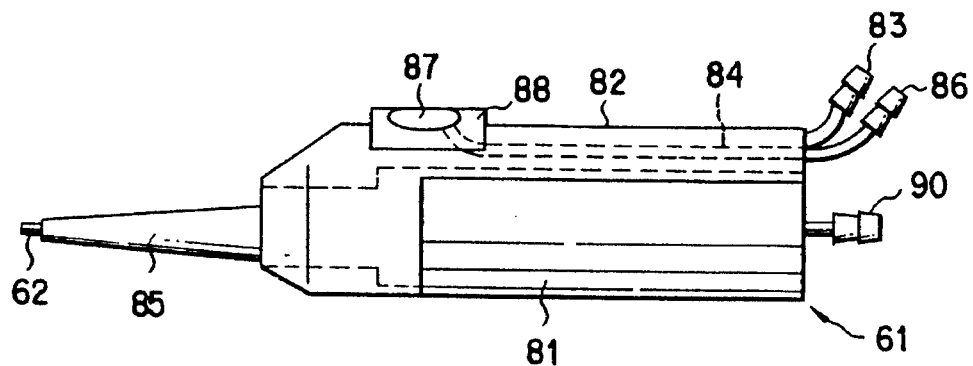
FIG. 13 is a schematic view showing a first embodiment of a hand piece to be connected to the apparatus of the invention.
Figure 14:
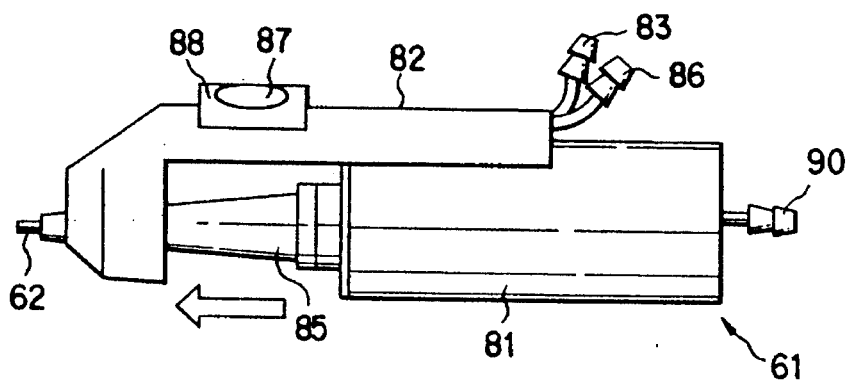
FIG. 14 is a schematic view showing the hand piece of FIG. 13 with its cover off.

FIG. 13 shows an arrangement in which a hand piece 61 is provided with a second cover 82 separate from a first cover 81 such that the second cover 82 can be axially removably fitted on the first cover 81. The second cover 82 is rotatable around the axis of the first cover 81.

The second cover 82 is provided with a water supply connector 83 and a suction adjusting connector 86. The connector 83 is designed so as to communicate with a water supply passage between a probe 62 and a sheath 85 surrounding the same when it is fitted with the second cover 82. Further, the second cover 82 is provided with a suction adjusting member 88 having a leakage port 87 which communicates with the suction adjusting connector 86 by means of a pressure pipe 84. The connector 86 is connected with a pressure adjusting tube which opens into the middle portion of a suction tube (not shown). Also, a suction connector 90 for connecting the suction tube is attached to the rear end of the first cover 81.

Normally, the hand piece 61 is used with the second cover 82 fitted thereon, as shown in FIG. 13. The suction pressure can be adjusted by regulating the opening of the leakage pot 87 of the suction adjusting member 88 by a finger.

If the suction pressure need not be adjusted, the hand piece 61 is used with the second cover 82 off. In this case, the hand piece 61 is fitted with the first cover 81 only, so that its grip portion is thinner and easier to handle than when the piece 61 is fitted also with the second cover 82. Moreover, the operation cannot be hindered by tubes which are connected to the water supply connector 83 and the suction adjusting connector 86 attached to the second cover 82.

FIG. 15 shows an arrangement in which a second cover 89 is provided with the water supply connector 83 only, and not with the suction adjusting connector 86 or the suction adjusting member 88. The second cover 89 of this type and the aforesaid second cover 82 can be alternatively fitted on the first cover 81.

The probe may be cooled by means of a dual-structure sheath which is composed of inner and outer sheaths fitted on the probe. In this arrangement, one of the gaps between the probe and the inner sheath and between the inner and outer sheaths is used as a water supply passage, and the other gap as a suction passage, the two passages communicating with each other at the respective distal ends of the sheaths. According to this arrangement, however, the gap between the probe and 10 the inner sheath serves as a suction passage 99 (see FIG. 16), so that blood and tissue pieces from an operated region are sucked into the gap. In some cases, a leakage hole 100, which communicates with a suction passage 93 in the bore of the probe, may be blocked. If the hole 100 is blocked, the probe cannot be cooled appropriately, and the fed fluid flows out directly into the operated region. As a result, the operated region is submerged, so that a satisfactory field of view cannot be enjoyed.

FIGS. 16 and 17 show an ultrasonic therapeutic apparatus which is arranged so as to solve the above problem. A probe 92, which is connected to a hand piece 91, is formed of a hollow member whose bore constitutes a first suction passage 93. The probe 9 is surrounded by a dual-structure sheath 96 which is formed inner and outer sheaths 94 and 95.

The gap between the inner and outer sheaths 94 and 95 of the dual-structure sheath 96 constitutes a water supply passage 97, which communicates with a water supply passage 98 of the hand piece 91. The gap between the inner sheath 94 and the probe 92 constitutes a second suction passage 99. The passage 99 communicates with the first suction passage 91 by means of the leakage hole 100 in the side wall of the probe 92. Also, the passage 99 is connected to a suction pump 103 by means of a suction tube 101 and a suction bottle 102, as shown in FIG. 17, so that sucked substances collect in the bottle 102.

A flow sensor 104, which is provided in the middle of the suction tube 101, continually observes the intake through the tube 101, and a signal from the sensor104 is fed back to a drive unit 105. Thus, in case of trouble, an alarm can be given, or the water supply or ultrasonic oscillation output can be stopped.

Normally, almost all the perfusate carried through the water supply passage 98 is recovered by suction through the second suction passage 99, leakage hole 100, and first suction passage 93. Thus, the quantity of the perfusate flowing out into the operation field through the distal end of the probe 92 can be minimized, so that the operation field can be kept in a favorable state.

If the leakage hole 100 is blocked by blood or tissue pieces, the perfusate can hardly be recovered through the second suction passage 99 and the hole 100, and almost all the perfusate inevitably flows out into the operation field through the distal end of the probe 92.

Thus, the intake through the suction tube 101 is less than in the normal state. A change of the intake is detected by means of the flow sensor 104, whereby he blocking of the leakage hole 100 can be recognized.

The flow sensor 104 may be provided in any other portion than the middle portion of the suction tube 101, provided it is situated on the suction pump side of the leakage hole 100. For example, the sensor 104 may be located in the suction passage 93 or near the suction bottle 102.

Since the blocking of the leakage hole 100 can be detected in this manner, the probe 92 can be prevented from being damaged, and the perfusate can be prevented from flowing out into the operation field and spoiling the field of vision.

Figure 18:
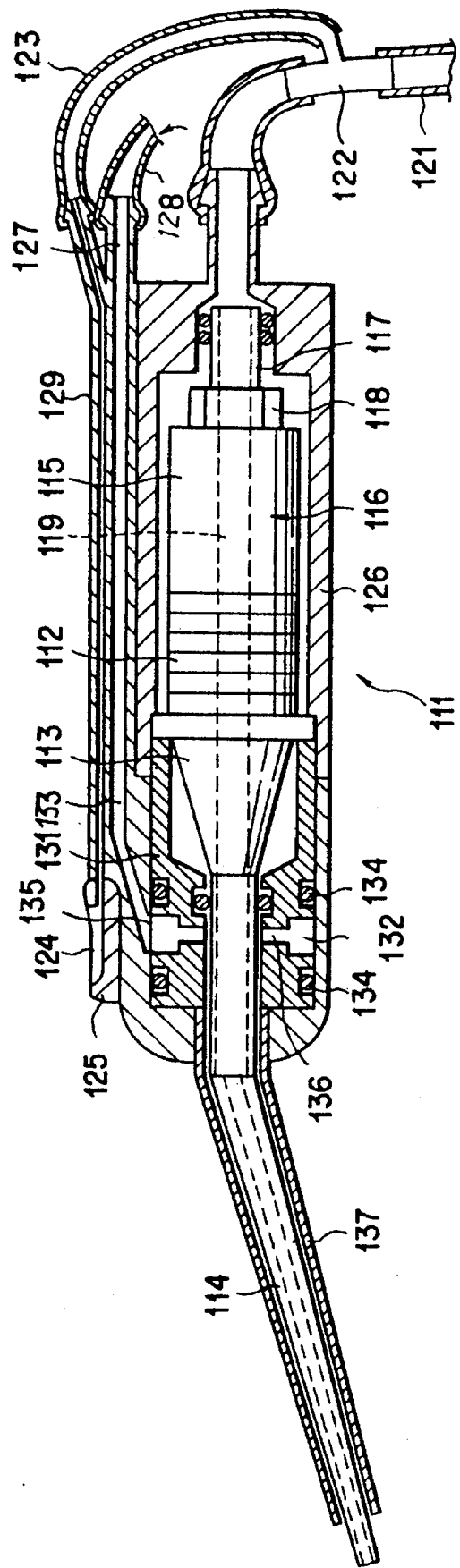
FIG. 18 is a sectional view showing a fourth embodiment of the hand piece to be connected to the apparatus of the invention.

FIG. 18 shows a hand piece 111 of another ultrasonic therapeutic apparatus. A horn 113 serves to enlarge the amplitude of axial ultrasonic vibration produced in an ultrasonic vibration element section 112 for generating ultrasonic vibration. The enlarged ultrasonic vibration is transmitted to an ultrasonic transmission member (probe) 114. The distal end of the transmission member 114 is used to cut or emulsify the affected tissue or crush a calculus.

Moreover, this ultrasonic therapeutic apparatus is provided with a lining plate 115 for sympathetic balance. The ultrasonic vibration element section 112, horn 113, and lining plate 115 are fixed together by means of a bolt 117 and a nut 118, thus constituting an integral ultrasonic vibrator section 116. The vibrator section 116 has a suction hole 119 therein, which communicates inside with the bolt 117, horn 113, and ultrasonic transmission member 114. A suction pump (not shown) communicates with the suction hole 119 by means of a suction tube 121. The cut or emulsified tissue or crushed calculus is removed by suction through the suction hole 119 by means of the sucking force of the suction pump.

For the manual control of the suction pressure, a connecting member 122 having a branch passage is provided in the middle of the suction tube 121 which communicates with the suction hole 119, and a flexible pressure tube 123, which communicates with the tube 121, is connected to the branch passage of the member 122.

The pressure tube 123 is connected to a suction pressure adjusting member. 125 which has a suction pressure adjusting hole 124. A suction leakage through the adjusting hole 124 can be controlled to adjust the suction pressure through the suction hole 119 by regulating the opening of the hole 124 with the bulb of a finger.

The suction pressure adjusting member 125 is mounted on a cover 126 of the hand piece 111. The cover 126 is provided with a water supply connector 127 for supplying a perfusate to a region to be subjected to ultrasonic treatment. A flexible water supply tube 128 is connected to the connector 127. The perfusate is fed pressurized to the connector 127 through the tube 128 by means of a feedwater pump (not shown). The adjusting member 125 is freely rotatable around the cover 126 of the hand piece 111 so that it can be handled in conformity to the size of the operator's hand or desired angle. The water supply connector 127 and the adjusting member 125 constitute an integral second cover 129. The second cover 129, which is rotatable around the cover 126, can be easily attached to and detached from the cover 126.

A manifold 131 is screwed in the front portion of the cover 126 so as to press a flange portion of the ultrasonic vibrator section 116. Thus held between the cover 126 and the manifold 131, the vibrator section 116 is fixed with respect to the cover 126. A circumferential groove is formed on the outer peripheral surface of the front portion of the manifold 131, and the second cover 129 is fitted on the manifold 131 from the front side so as to cover the groove 132. An O-ring 134 is provided on each side of the groove 132, whereby the interface between the second cover 129 and the manifold 131 is kept watertight. An outlet 135 of a water supply passage 133 in the second cover 129, which communicates with the inside of the water supply connector 127, is situated corresponding to the groove 132 of the manifold 131. A hole 136 is bored through the base of the groove 132 so as open into the bore of the manifold 131. The perfusate flows out into the groove 132 through the outlet 135 of the water supply passage 133 in the second cover 129, and then gets into the bore of the manifold 131 through the hole 136. A sheath 137 is fixedly screwed to the front of the manifold 131. The manifold 131 and the sheath 137 are penetrated by the horn 113 and the ultrasonic transmission member 114 continuous therewith. The perfusate is fed through a passage defined between the transmission member 114 and the sheath 137.

Also available is a second cover (not shown) which is furnished with water supply means without including a suction pressure adjusting member. This second cover and the second cover 129 are freely replaceable with each other.

As described above, the second cover 129, along with the suction pressure adjusting member 125, can freely rotate around the cover 126, so that the operator can perform a surgical operation with the grip adjusted to the size of his or her hand or desired angle before or during the operation. When the adjusting member 125 is rotated, moreover, the water supply connector 127 rotates together around the outer peripheral surface of the first cover 126. Accordingly, the pressure tube 123 and the water supply tube 128, which are connected to the adjusting member 125 and the connector 127, respectively, simultaneously rotate around the cover 126 without getting tangled together. Since the second cover can be easily replaced with the one which is furnished with the water supply means without including the suction pressure adjusting member, furthermore, the adjusting member 125 never hinders the grip on the hand piece 111 in the case of a surgical operation which requires no suction pressure adjustment.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A method of setting a value of an output from an ultrasonic therapeutic apparatus and of treating an organic tissue by means of the ultrasonic therapeutic apparatus, wherein the ultrasonic therapeutic apparatus comprises an ultrasonic apparatus main body including a source of ultrasonic oscillations to produce ultrasonic waves, a hand piece removably connected to the ultrasonic apparatus main body, a probe which contacts an organic tissue and which is removably connected to the hand piece, and a cooling water supply which supplies cooling water to the probe, the method comprising the steps of:

detecting whether or not a handpiece is connected to an ultrasonic apparatus main body;

feeding cooling water to a probe connected to the hand piece when it is detected that the hand piece is connected to the ultrasonic apparatus main body;

detecting whether or not a feedwater output value is fed to the probe; and then establishing a state where ultrasonic waves can be outputted to the probe so that ultrasonic treatment of organic tissue can be performed after said feedwater output value is fed to the probe.

2. The method according to claim 1, further comprising the step of urging an operator to feed cooling water to a probe beforehand, after detection of connection of a hand piece to the ultrasonic apparatus main body.

3. A method according to claim 1, wherein when it is detected that a handpiece is not connected to the ultrasonic apparatus main body, an instruction for an operator to connect a hand piece is displayed.

* * * * *